US012370585B2

(12) United States Patent
Dubois

(10) Patent No.: US 12,370,585 B2
(45) Date of Patent: Jul. 29, 2025

(54) METHOD FOR RECOVERING AND SEPARATING UNSATURATED FLUORINATED HYDROCARBONS

(71) Applicant: ARKEMA FRANCE, Colombes (FR)

(72) Inventor: Jean-Luc Dubois, Colombes (FR)

(73) Assignee: ARKEMA FRANCE, Colombes (FR)

( * ) Notice: Subject to any disclaimer, the term of this patent is extended or adjusted under 35 U.S.C. 154(b) by 741 days.

(21) Appl. No.: 17/639,373

(22) PCT Filed: Sep. 4, 2020

(86) PCT No.: PCT/EP2020/074783
§ 371 (c)(1),
(2) Date: Mar. 1, 2022

(87) PCT Pub. No.: WO2021/043991
PCT Pub. Date: Mar. 11, 2021

(65) Prior Publication Data
US 2022/0267237 A1    Aug. 25, 2022

(30) Foreign Application Priority Data
Sep. 6, 2019  (FR) .................................. FR1909815

(51) Int. Cl.
| C07C 17/38 | (2006.01) |
| B01D 11/02 | (2006.01) |
| B09B 3/10 | (2022.01) |
| B09B 3/32 | (2022.01) |
| B09B 3/35 | (2022.01) |
| B09B 3/80 | (2022.01) |
| C07C 17/383 | (2006.01) |

(52) U.S. Cl.
CPC .......... *C07C 17/38* (2013.01); *B01D 11/0288* (2013.01); *B09B 3/10* (2022.01); *B09B 3/32* (2022.01); *B09B 3/35* (2022.01); *B09B 3/80* (2022.01); *C07C 17/383* (2013.01)

(58) Field of Classification Search
CPC ... C07C 17/38; C07C 17/383; B01D 11/0288; B09B 3/10; B09B 3/32; B09B 3/35; B09B 3/80
See application file for complete search history.

(56) References Cited

U.S. PATENT DOCUMENTS

| 4,976,862 | A | * | 12/1990 | Ascough ................. C08J 11/02 |
| | | | | 95/143 |
| 6,432,512 | B1 | * | 8/2002 | Brandolini .......... B29C 44/5609 |
| | | | | 428/316.6 |
| 2006/0200964 | A1 | | 9/2006 | Cameron et al. |
| 2012/0059200 | A1 | | 3/2012 | Pokrovski et al. |
| 2016/0130416 | A1 | * | 5/2016 | Chen ...................... C08J 9/0061 |
| | | | | 521/128 |

FOREIGN PATENT DOCUMENTS

| CN | 1069269 | A | 2/1993 |
| CN | 2337148 | Y | 9/1999 |
| CN | 100998986 | A | 7/2007 |
| CN | 106807723 | A | 6/2017 |
| EP | 0392760 | A2 | 10/1990 |
| EP | 0526002 | A2 | 7/1992 |
| EP | 0514106 | A2 | 11/1992 |
| EP | 0636429 | A2 | 2/1995 |
| JP | H11199702 | A | 7/1999 |
| JP | 2004143464 | A | 5/2004 |
| JP | 2014028801 | A | 2/2014 |
| WO | 9322077 | A1 | 11/1993 |
| WO | 0202209 | A2 | 1/2002 |
| WO | 2014193689 | A1 | 12/2014 |

OTHER PUBLICATIONS

ISA/EP; International Search Report and Written Opinion for International Patent Application No. PCT/EP2020/0174783 dated Nov. 20, 2020, 17 pages.

* cited by examiner

*Primary Examiner* — Jafar F Parsa
(74) *Attorney, Agent, or Firm* — NK Patent Law

(57) ABSTRACT

A process for recovering and upgrading unsaturated fluorinated hydrocarbons, comprises: a) providing a foam M1 consisting of pores containing a composition C1 comprising at least one unsaturated fluorinated hydrocarbon; b1) optionally grinding or compressing said foam M1 to form a ground foam or a compressed foam; b2) optionally recovering at least a portion of said composition C1; c) depolymerizing or dissolving said foam M1 provided in step a) or said ground or compressed foam obtained in step b1); d) recovering at least a portion of said composition C1 and optionally mixing the latter with said at least a portion of the composition recovered in step b2) to form a stream A comprising at least one unsaturated fluorinated hydrocarbon; e) recovering and separating said stream A into a plurality of streams of which at least one stream B1 comprises said at least one unsaturated fluorinated hydrocarbon.

19 Claims, No Drawings

METHOD FOR RECOVERING AND SEPARATING UNSATURATED FLUORINATED HYDROCARBONS

CROSS-REFERENCE TO RELATED APPLICATIONS

This application is a U.S. National Stage application of International Patent Application No. PCT/EP2020/074783, filed on Sep. 4, 2020, which claims the benefit of French Patent Application No. FR1909815, filed on Sep. 6, 2019.

TECHNICAL FIELD OF THE INVENTION

The present invention relates to a process for recovering and separating unsaturated fluorinated hydrocarbons. In particular, the present invention relates to a process for recovering and separating unsaturated fluorinated hydrocarbons present in insulating foams.

TECHNOLOGICAL BACKGROUND OF THE INVENTION

The disposal or recycling of refrigerators involves the removal of bulky waste and delivery thereof to specific reprocessing plants. The scrapping of this type of device is known in particular from DE2850130. This involves in particular crushing the various elements, separating them, and then recycling the various materials where possible.

In particular, refrigerators contain insulating foams generally made from a polyurethane-based polymer. These foams also contain blowing agents. The blowing agent compositions used comprise in particular halohydrocarbons.

Since legislation concerning halohydrocarbon derivatives has evolved over time, devices containing insulating foams may contain CFCs (chlorofluorocarbons), HFCs (hydrofluorocarbons) or HFOs (hydrofluoroolefins). Indeed, hydrofluoroolefins are attracting attention because they offer promising behavior with a low global warming potential. There is therefore a need for processing and recycling devices containing insulating foams containing the new generations of blowing agents, but also a need to process and recycle devices containing insulating foams regardless of the generation of blowing agents used.

SUMMARY OF THE INVENTION

The present invention relates to a process for recovering and upgrading unsaturated fluorinated hydrocarbons, comprising the steps of:
a) providing a foam M1 consisting of pores containing a composition C1 comprising at least one unsaturated fluorinated hydrocarbon;
b1) optionally grinding or compressing said foam M1 provided in step a) to form a ground foam or a compressed foam;
b2) optionally recovering at least a portion of said composition C1 comprising at least one unsaturated fluorinated hydrocarbon and released during step b1);
c) depolymerizing or dissolving said foam M1 provided in step a) or said ground or compressed foam obtained in step b1);
d) recovering at least a portion of said composition C1 comprising at least one unsaturated fluorinated hydrocarbon and released during step c) and optionally mixing the latter with said at least a portion of the composition recovered in step b2) to form a stream A comprising at least one unsaturated fluorinated hydrocarbon;
e) recovering and separating said stream A formed in step d) into a plurality of streams of which at least one stream B1 comprises said at least one unsaturated fluorinated hydrocarbon.

According to a preferred embodiment, the unsaturated fluorinated hydrocarbon comprises three or four carbon atoms.

According to a preferred embodiment, said unsaturated fluorinated hydrocarbon contains a single carbon-carbon double bond.

According to a preferred embodiment, said foam M1 consists of polyurethane, polyolefin, poly(methyl methacrylate), polyhydroxyalkanoate, polylactic acid, polyimide, poly(vinyl chloride), poly(ethylene/vinyl acetate), poly(etherimide), poly(methacrylimide), polycarbonate or polystyrene, or a mixture thereof, preferably the foam consists of polyurethane, polyolefin, poly(methyl methacrylate) or polystyrene.

According to another preferred embodiment, said foam M1 provided in step a) consists of polystyrene; and step c) is carried out in the presence of an organic solvent capable of dissolving the polystyrene or step c) is carried out by thermal depolymerization of the polystyrene.

According to a preferred embodiment, said foam M1 provided in step a) consists of polyurethane and step c) is carried out by an alcoholysis or hydrolysis or ammonolysis or aminolysis reaction.

In the context of the present invention, "ammonolysis reaction" refers to the reaction of the polyurethane with $NH_3$. "Aminolysis reaction" refers to the reaction of the polyurethane with a primary amine or a secondary amine.

According to a preferred embodiment, step c) results in the formation of polyol compounds, the latter being recovered, purified and recycled into a process for the production of polyurethane.

According to a preferred embodiment, step e) of separating said stream is carried out by distillation, azeotropic distillation, pressurized distillation, extractive distillation, cold separation, absorption in a solvent, or a combination thereof.

According to a preferred embodiment, said stream A is subjected to a step of adsorption prior to step e) or said stream B1 is subjected to a step of adsorption after step e).

According to a preferred embodiment, said at least one unsaturated fluorinated hydrocarbon included in said composition C1 is selected from the group consisting of 3,3,3-trifluoropropene, 2,3,3,3-tetrafluoropropene, (E/Z)-1,3,3,3-tetrafluoropropene, (E/Z)-1,2,3,3,3-pentafluoropropene, 2-chloro-3,3,3-trifluoropropene, 1-chloro-3,3,3-trifluoropropene, 1,1-dichloro-3,3,3-trifluoropropene and 1,2-dichloro-3,3,3-trifluoropropene, (E/Z)-1,1,1,4,4,4-hexafluorobut-2-ene, 2,4,4,4-tetrafluorobut-1-ene, and mixtures thereof.

According to a preferred embodiment, said composition C1 also comprises a hydrofluorocarbon other than said at least one unsaturated fluorinated hydrocarbon, an alkane, methyl formate, an inert gas, an alcohol, an ether, a fluorinated ether, an unsaturated fluorinated ether, a ketone, a fluoroketone, a chlorofluorocarbon or water, or a mixture thereof.

According to a preferred embodiment, said hydrofluorocarbon other than said at least one unsaturated fluorinated hydrocarbon is selected from the group consisting of difluoromethane (HFC-32), fluoroethane (HFC-161), 1,2-difluoroethane (HFC-152), 1,1-difluoroethane (HFC-152a), 1,1,2-trifluoroethane (HFC-143), 1,1,1-trifluoroethane (HFC-143a), 1,1,2,2-tetrafluoroethane (HFC-134), 1,1,1,2-tetrafluoroethane (HFC-134a), 1,1,1,2,2-pentafluoroethane (HFC-125), 1,1,1,3,3-pentafluoropropane (HFC-245fa), 1,1,1,3,3,3-hexafluoropropane (HFC-236fa), 1,1,2,3,3,3-hexafluoropropane (HFC-236ea), 1,1,1,3,3-pentafluorobutane (HFC-365mfc), 1,1,1,2,3,3,3-heptafluoropropane (HFC-227ea).

According to a preferred embodiment, said chlorofluorocarbon is selected from the group consisting of trichlorofluoromethane, dichlorodifluoromethane, trichlorotrifluoroethane, dichlorotetrafluoroethane, chloropentafluoroethane.

According to a preferred embodiment, said stream A comprises a content of said at least one fluorinated hydrocarbon of between 50% and 99% by volume, based on the total volume of said stream A.

According to another preferred embodiment, step a) also comprises:
  providing a foam M2 consisting of pores containing a composition C2 comprising a hydrofluorocarbon selected from the group consisting of difluoromethane (HFC-32), fluoroethane (HFC-161), 1,2-difluoroethane (HFC-152), 1,1-difluoroethane (HFC-152a), 1,1,2-trifluoroethane (HFC-143), 1,1,1-trifluoroethane (HFC-143a), 1,1,2,2-tetrafluoroethane (HFC-134), 1,1,1,2-tetrafluoroethane (HFC-134a), 1,1,1,2,2-pentafluoroethane (HFC-125), 1,1,1,3,3-pentafluoropropane (HFC-245fa), 1,1,1,3,3,3-hexafluoropropane (HFC-236fa), 1,1,2,3,3,3-hexafluoropropane (HFC-236ea), 1,1,1,3,3-pentafluorobutane (HFC-365mfc), 1,1,1,2,3,3,3-heptafluoropropane (HFC-227ea), or
  providing a foam M3 consisting of pores containing a composition C3 comprising a chlorofluorocarbon selected from the group consisting of trichlorofluoromethane, dichlorodifluoromethane, trichlorotrifluoroethane, dichlorotetrafluoroethane, chloropentafluoroethane, or
  providing a mixture of said foams M2 and M3.

According to a preferred embodiment, the foam M2 and the foam M3 consist of a polymer identical to that of said foam M1.

According to a preferred embodiment, the composition C2 and the composition C3 are devoid of unsaturated fluorinated hydrocarbon.

According to this other preferred embodiment, said process comprises the steps of:
  b1) optionally grinding or compressing said foam M1, said foam M2 and/or said foam M3 provided in step a) to form a ground foam or a compressed foam;
  b2) optionally recovering at least a portion of said composition C1 and at least a portion of said composition C2 and/or at least a portion of said composition C3, released during step b1);
  c) depolymerizing or dissolving said foam M1 and said foam M2 and/or said foam M3 provided in step a) or said ground or compressed foam obtained in step b1);
  d) recovering at least a portion of said composition C1 and at least a portion of said composition C2 and/or at least a portion of said composition C3, released during step c), and optionally mixing them with those recovered in step b2) to form a stream A;
  e) recovering and separating said stream A into a plurality of streams of which at least one stream B1 comprises said at least one unsaturated fluorinated hydrocarbon.

According to this other preferred embodiment, said stream A comprises a content of said at least one fluorinated hydrocarbon of between 0.1% and 50% by volume, based on the total volume of said stream A.

DETAILED DESCRIPTION OF THE INVENTION

The present invention relates to a process for recovering and upgrading fluorinated hydrocarbons. The term "unsaturated fluorinated hydrocarbon" denotes a hydrocarbon compound comprising at least one fluorine atom on its carbon chain and at least one carbon-carbon double bond. The unsaturated fluorinated hydrocarbon may contain two, three or four carbon atoms. Preferably, the unsaturated fluorinated hydrocarbon comprises three or four carbon atoms and one carbon-carbon double bond.

Preferably, the present process comprises in particular the step of:
  a) providing a foam M1 consisting of pores containing a composition C1 comprising at least one unsaturated fluorinated hydrocarbon. Said foam is for example obtained from devices such as refrigerators, freezers, cold storage devices, LNG tankers (transport of liquefied gas). As described in the prior art, devices containing foam are recycled via a first step of disassembling said devices in order to sort the different constituents. For example, in refrigerating devices, the refrigerant composition contained in the cooling circuit is suctioned off in order to be recycled in parallel. The various components, such as the motor, the refrigeration unit, the switches, the ferrous or nonferrous heavy metals, the aluminum, are removed and sent or transported to specific sorting systems. Once the various elements have been sorted, the foam is recovered and processed according to the steps described in the present process. Said foam is a porous material. Said pores present in the foam contain a composition C1 comprising at least one unsaturated fluorinated hydrocarbon. However, the composition containing at least one unsaturated fluorinated hydrocarbon remains absorbed by the foam as such over the course of time. The present invention makes it possible to maximize the recovery of said composition containing at least one unsaturated fluorinated hydrocarbon.

According to a preferred embodiment, said at least one unsaturated fluorinated hydrocarbon included in said composition C1 is selected from the group consisting of 3,3,3-trifluoropropene, 2,3,3,3-tetrafluoropropene, (E/Z)-1,3,3,3-tetrafluoropropene, (E/Z)-1,2,3,3,3-pentafluoropropene, 2-chloro-3,3,3-trifluoropropene, 1-chloro-3,3,3-trifluoropropene, 1,1-dichloro-3,3,3-trifluoropropene and 1,2-dichloro-3,3,3-trifluoropropene, (E/Z)-1,1,1,4,4,4-hexafluorobut-2-ene, 2,4,4,4-tetrafluorobut-1-ene, and mixtures thereof. In particular, said unsaturated fluorinated hydrocarbon is 1-chloro-3,3,3-trifluoropropene.

According to a preferred embodiment, said composition C1 may also comprise a hydrofluorocarbon other than said at least one fluorinated hydrocarbon, an alkane, carbon dioxide, methyl formate, an inert gas, an alcohol, an ether, a fluorinated ether, an unsaturated fluorinated ether, a ketone, a fluoroketone, a chlorofluorocarbon or water, or a mixture thereof. Said hydrofluorocarbon other than said at least one fluorinated hydrocarbon may be selected from the group consisting of difluoromethane (HFC-32), fluoroethane (HFC-161), 1,2-difluoroethane (HFC-152), 1,1-difluoroethane (HFC-152a), 1,1,2-trifluoroethane (HFC-143), 1,1,1- trifluoroethane (HFC-143a), 1,1,2,2-tetrafluoroethane (HFC-134), 1,1,1,2-tetrafluoroethane (HFC-134a), 1,1,1,2,2-pentafluoroethane (HFC-125), 1,1,1,3,3-pentafluoropropane (HFC-245fa), 1,1,1,3,3,3-hexafluoropropane (HFC-236fa), 1,1,2,3,3,3-hexafluoropropane (HFC-236ea), 1,1,1,3,3-pentafluorobutane (HFC-365mfc), 1,1,1,2,3,3,3-heptafluoropropane (HFC-227ea).

Preferably, said chlorofluorocarbon is selected from the group consisting of trichlorofluoromethane, dichlorodifluoromethane, trichlorotrifluoroethane, dichlorotetrafluoroethane and chloropentafluoroethane.

According to a particular embodiment, the present process may comprise the steps of:
b1) optionally grinding or compressing said foam M1 provided in step a) to form a ground or compressed foam;
b2) optionally recovering at least a portion of said composition C1 comprising at least one unsaturated fluorinated hydrocarbon and released during step b1).

Said step b1) can be carried out using suitable grinders or compressing machines known to those skilled in the art. Said grinding is carried out so as to obtain a ground foam. Said compression is carried out so as to obtain a compressed and densified foam. The grinding or compression of the foam leads to the release of at least a portion of said composition comprising at least one fluorinated hydrocarbon. The ground foam may be of variable shape and dimensions. According to a preferred embodiment, the ground foam has a dimension of between 0.05 cm and 15 cm. Said dimension expressed here is the greatest dimension of said ground foam. Below 0.05 cm, said foam may degrade and possibly soften or melt. Beyond 15 cm, the release of said composition is not optimal. Preferably, the ground foam has a dimension of between 0.1 cm and 14 cm, advantageously the ground foam has a dimension of between 0.1 cm and 13 cm, preferably the ground foam has a dimension of between 0.5 cm and 12 cm, more preferentially the ground foam has a dimension of between 1 cm and 11 cm, in particular the ground foam has a dimension of between 1 and 5 cm.

As mentioned above, during this step b1) of grinding or compression, said composition C1 comprising at least one unsaturated fluorinated hydrocarbon contained in said foam M1 will be at least partly released. Thus, during step b2), at least a portion of said composition C1 comprising at least one unsaturated fluorinated hydrocarbon and released during step b1) is recovered. Said at least a portion of said composition C1 may be recovered by a suction device. Preferably, steps b1) and b2) are carried out in a hermetically sealed processing chamber comprising said suction device. The latter comprises at least one or more suction nozzles capable of recovering at least a portion of said composition C1 comprising at least one unsaturated fluorinated hydrocarbon and released during the grinding or compression step b1).

According to a particular embodiment, said foam M1 is placed under partial vacuum prior to carrying out step b1). This makes it possible to evacuate the air surrounding it. Preferably, said foam is placed under a pressure of less than 0.9 bar relative and greater than 0.1 bar relative, preferably under a pressure of less than 0.8 bar relative and greater than 0.2 bar relative.

Said at least a portion of said composition C1 comprising at least one unsaturated fluorinated hydrocarbon recovered in step b2) may be purified. Said purification may be carried out by passing said at least a portion of said composition C1 comprising at least one unsaturated fluorinated hydrocarbon through dust filters. Said dust filters may have pores having a size varying between 0.5 μm and 10 μm. This purification step makes it possible to remove any particles that have been suctioned up alongside said at least a portion of said composition C1 comprising at least one unsaturated fluorinated hydrocarbon. Subsequently to this purification step, said at least a portion of said composition C1 comprising at least one unsaturated fluorinated hydrocarbon may be stored before subsequently being processed as will be described in the present application in steps d) and e).

The foam provided in step a) and the ground or compressed foam in step b1), if steps b1) and b2) have been carried out, can be collected together to be processed according to step c) of the present process.

Said process thus comprises a step c) of:
c) depolymerizing or dissolving the foam M1 provided in step a) and/or said ground or compressed foam obtained in step b1).

The choice between depolymerization and dissolution depends on the type of foams to be processed. Those skilled in the art will know how to identify the most suitable technique by way of their general knowledge. For example, when a polyurethane foam is to be processed in step c), depolymerization will be favored. In contrast, when a polystyrene foam is to be processed in step c), dissolution and depolymerization can be considered.

According to a preferred embodiment, said foam M1 consists of polyurethane, polyolefin, poly(methyl methacrylate), polyhydroxyalkanoate, polylactic acid, polyimide, poly(vinyl chloride), poly(ethylene/vinyl acetate), poly(etherimide), poly(methacrylimide), polycarbonate or polystyrene, or a mixture thereof, preferably the foam consists of polyurethane, polyolefin, poly(methyl methacrylate) or polystyrene.

Preferably, said foam consists of polyurethane. Polyurethane foam as described herein encompasses polymers comprising only polyurethane units and also copolymers comprising polyurethane units. Preferably, said polyurethane foam comprises at least 20% by weight of polyurethane units based on the total weight of said foam. According to a preferred embodiment, said polyurethane foam comprises at least 30% by weight of polyurethane units based on the total weight of said foam, advantageously at least 40% by weight of polyurethane units based on the total weight of said foam, preferably at least 50% by weight of polyurethane units based on the total weight of said foam, more preferentially at least 60% by weight of polyurethane units based on the total weight of said foam, in particular at least 70% by weight of polyurethane units based on the total weight of said foam, more particularly at least 80% by weight of polyurethane units based on the total weight of said foam.

According to the present invention, the term "polyurethane units" refers to a compound comprising the unit —[$R^1$—NH—CO—O—$R^2$]n- in which the substituents $R^1$ and $R^2$ can be selected from the group consisting of $C_1$-$C_{30}$ alkyl, $C_2$-$C_{30}$ alkenyl, $C_6$-$C_{30}$ aryl; and n is greater than 3, preferably greater than 10, in particular greater than 50. The term "alkyl" means a linear or branched alkyl group containing at least 1 and at most 30 carbon atoms. The alkyl group may be substituted by an unsubstituted aryl group, OH, $C_1$-$C_{10}$ alkoxy, or a carbonyl or carboxyl group. The term "alkenyl" means a linear or branched alkenyl group containing at least 2 and at most 30 carbon atoms. The alkenyl group comprises at least one carbon-carbon double bond. The alkenyl group may comprise two or three carbon-carbon double bonds. The alkenyl group may be substituted by an unsubstituted aryl group, OH, $C_1$-$C_{10}$ alkoxy, or a carbonyl or carboxyl group. The term "aryl" refers to an aromatic hydrocarbon ring containing the specified number of carbon atoms and which is unsubstituted or substituted by an unsubstituted $C_1$-$C_{10}$ alkyl, a carbonyl, carboxyl, OH, or $C_1$-$C_{10}$ alkoxy group.

When the foam employed in the process is a polyurethane foam, step c) preferably implements a depolymerization step. Said depolymerization may be carried out by alcoholysis, hydrolysis, ammonolysis or aminolysis reactions.

The alcoholysis reaction comprises bringing the, optionally ground or compressed, but preferably ground or compressed, polyurethane foam into contact with an alcohol. Preferably, the alcohol has a boiling point of between 30° C. and 350° C., advantageously between 50° C. and 325° C., preferably between 60° C. and 300° C. Preferably, the alcohol is selected from glycerol, methanol or a glycol compound. Preferably, said glycol compound has a molecular weight of less than 1000 g/mol, in particular less than 500 g/mol. According to a preferred embodiment, the glycol compound is selected from the group consisting of ethylene glycol, diethylene glycol, triethylene glycol, tetraethylene glycol, 1,3-propylene glycol, 1,2-propylene glycol, di-, tri-, tetra-1,2-propylene glycol, butanediol and hexanediol. The molar ratio between the alcohol and the unit —[$R^1$—NH—CO—O—$R^2$]— is between 1/1 and 5/1, advantageously between 1/1 and 4/1, preferably between 1/1 and 3/1, in particular between 1/1 and 2/1. Said alcoholysis reaction may be carried out in the presence of an amine of the formula $R^3{}_n NH_{3-n}$ in which $R^3$ is an alkyl radical comprising from 1 to 10 carbon atoms, optionally substituted by one or more OH groups or one or more $NH_2$ groups; and n is 1 or 2. If the amine comprises several groups $R^3$ as defined above, these may be identical or different or linked together to form a heterocycle. Preferably, said amine is of the formula $R^3{}_n NH_{3-n}$ in which $R^3$ is an alkyl radical comprising from 1 to 4 carbon atoms and substituted by one or more OH groups or one or more $NH_2$ groups; n being as defined above. In particular, said amine may be a compound having a molecular weight of less than 200 g/mol, preferably less than 150 g/mol. More particularly, said amine may be selected from methanolamine, ethanolamine, diethanolamine, dipropanolamine and triethanolamine, and combinations thereof. Alternatively, said amine may be HMTA (i.e. hexamethylenetetramine). The alcoholysis reaction may also be carried out in the presence of a catalyst. Said catalyst may be an acetate of an alkali metal such as lithium acetate, sodium acetate or potassium acetate. The amount of catalyst may be between 0.01% and 5% relative to the weight of polyurethane foam, advantageously between 0.1% and 5% by weight, preferably between 0.5% and 5% by weight and more preferentially between 1% and 5% by weight. Carrying out the depolymerization by alcoholysis results in the formation of polyol compounds and possibly urethane compounds.

The hydrolysis reaction comprises bringing the, optionally ground or compressed, but preferably ground or compressed, polyurethane foam into contact with water. The step of depolymerization of polyurethane foam by hydrolysis is preferably carried out at high pressure, advantageously at a pressure of greater than 2 bar absolute, preferably greater than 5 bar absolute, in particular greater than 10 bar absolute. The step of depolymerization of polyurethane foam by hydrolysis is preferably carried out at a temperature of from 100° C. to 300° C., preferably from 150° C. to 300° C. Thus, the water is at least partly in the form of water vapor. The reaction time for this hydrolysis step is from 1 minute to 5 hours, preferably from 5 minutes to 2 hours, in particular from 10 minutes to 1 hour. Carrying out the depolymerization by hydrolysis results in the formation of polyol compounds, amine compounds and $CO_2$.

The step of depolymerization of polyurethane foams may be carried out by decomposition in the presence of $NH_3$ (ammonolysis reaction), or of a primary amine or a secondary amine (aminolysis reaction). The primary or secondary amine is preferably of the formula $R^4 R^5 R^6 N$ in which $R^4$, $R^5$ and $R^6$ are each independently selected from H, $C_1$-$C_{10}$ alkyl which is unsubstituted or substituted by an $NH_2$ group, and $C_1$-$C_{10}$ alkenyl which is unsubstituted or substituted by an $NH_2$ group, preferably H, $C_1$-$C_5$ alkyl which is unsubstituted or substituted by an $NH_2$ group, and $C_1$-$C_5$ alkenyl which is unsubstituted or substituted by an $NH_2$ group; with the proviso that at least one of the groups $R^4$, $R^5$ and $R^6$ represents a hydrogen and that $R^4$, $R^5$ and $R^6$ are not simultaneously hydrogen. In particular, the amine may be diethylenetriamine, triethylenetetramine. This step may be carried out at a temperature of between 50° C. and 300° C., preferably between 100° C. and 250° C. The step of depolymerization by reaction with an amine results in the formation of polyol compounds and amines.

Regardless of the method used for the step of depolymerization of the polyurethane foams, the present process may comprise a step of recovery and purification of the polyol compounds formed during step c). The purification of the polyol compounds may be carried out by distillation, centrifugation or by extraction in the presence of a solvent. After purification, the purified polyol compounds are preferably used in a process for the production of polyurethane. According to another preferred embodiment, said foam consists of polystyrene. In this case, step c) is carried out by bringing said polystyrene foam into contact with an organic solvent capable of dissolving said foam. In the present invention, the term "polystyrene" refers to a polymer or a copolymer comprising at least one unit of formula —[$CH_2 CH(C_6 R^7{}_5)]_n$— in which $C_6 R^7{}_5$ represents an aromatic carbon ring in which $R^7$ is independently H or a $C_1$-$C_5$ alkyl; and in which n is greater than 3, preferably greater than 10, in particular greater than 50. Preferably, this dissolution step may be carried out at a temperature ranging from 10° C. to 150° C., preferably from 20° C. to 100° C. According to a preferred embodiment, said organic solvent is selected from the group consisting of n-octane, n-dodecane, cyclohexane, methylcyclohexane, benzene, toluene, naphthalene, styrene, o-xylene, ethylbenzene, p-diethylbenzene, p-cymene, chloromethane, 1,1-dichloroethylene, ethylene dichloride, chloroform, 1,1-dichloroethane, trichloroethylene, carbon tetrachloride, chlorobenzene, o-dichlorobenzene, tetrahydrofuran, 1,4-dioxane, dibenzyl ether, acetone, methyl ethyl ketone, cyclohexanone, diethyl ketone, acetophenone, methyl isobutyl ketone, methyl isoamyl ketone, isophorone, di(isobutyl) ketone, methyl acetate, ethyl formate, 1,2-propylene carbonate, ethyl acetate, diethyl carbonate, n-butyl acetate, 2-ethoxyethyl acetate, isoamyl acetate, 2-nitropropane, nitrobenzene, ethylenediamine, pyridine, morpholine, aniline, N-methyl-2-pyrrolidone, cyclohexylamine, quinoline, N,N-dimethylformamide, carbon disulfide, dimethyl sulfoxide, ethanediol, ethanol, allyl alcohol, 1-propanol, 2-propanol, 1-butanol, 2-butanol, benzyl alcohol, cyclohexanol, diacetone alcohol, ethylene glycol monoethyl ether, diethylene glycol monomethyl ether, diethylene glycol monoethyl ether, ethylene glycol monobutyl ether, diethylene glycol monobutyl ether, 1-decanol, benzoic acid, stearic acid, phenol, resorcinol, m-cresol, methyl salicylate, ethylene glycol, glycerol and propylene glycol, or a mixture thereof.

The contacting of the organic solvent with the polystyrene foam results in the formation of a liquid phase L containing said organic solvent and dissolved polystyrene. A mixture of two or more organic solvents as mentioned above may be considered since said liquid phase L changes over time due to the dissolution of the polystyrene therein; i.e. the liquid phase L will become concentrated in polystyrene. Thus, a solvent may be capable of dissolving the polystyrene when the liquid phase does not have a high concentration of the latter, but may no longer be capable of dissolving the polystyrene when the liquid phase becomes more concentrated in polystyrene. It may therefore be useful to use a mixture of solvents, one of the solvents of which makes it possible to dissolve the polystyrene in a low-concentration liquid phase and the other solvent of which makes it possible to dissolve the polystyrene in a more concentrated liquid phase. Thus, the mixture of organic solvents may be selected so as to enable dissolution of the polystyrene whatever the polystyrene concentration in the liquid phase L. This liquid phase L may be subsequently purified. The purification of this liquid phase L for example includes a step of distillation, of filtration and/or precipitation by contact with a nonsolvent. Distillation may be used when a mixture of organic solvents is used, in particular when the organic solvents form an azeotropic mixture. The latter may be recovered and recycled in order to again be brought into contact with polystyrene. Filtration makes it possible to remove residues which are insoluble in said organic solvent. The purification may also include a subsequent step of precipitation and washing. Thus, the liquid phase L is preferably brought into contact with a nonsolvent capable of precipitating the polystyrene contained in the liquid phase L. The organic solvent(s) and the nonsolvent are recovered, separated and recycled. Preferably, the organic solvent(s) and the nonsolvent are identical and are capable of dissolving or precipitating the polystyrene depending on the pressure and temperature conditions. It will therefore suffice to vary the pressure and temperature conditions to precipitate the polystyrene and recover the organic solvent(s). The polystyrene thus precipitated is then subjected to one or more steps of washing with said nonsolvent. The volume ratio between the nonsolvent and the liquid phase L is from 2:1 to 4:1. Said nonsolvent is preferably a linear or branched $C_6$-$C_{10}$ alkane, in particular a linear or branched $C_6$-$C_8$ alkane. The washing step(s) are generally followed by a step of drying of said precipitated polystyrene at a temperature of between 100° C. and 130° C., preferably between 115° C. and 125° C.

According to another embodiment, said foam consisting of polystyrene may be depolymerized in step c). The depolymerization of the polystyrene is preferably carried out thermally. Thus, said foam consisting of polystyrene is preferably heated to a temperature of between 200° C. and 500° C. At such a temperature, the polystyrene is in the molten state and then depolymerizes. According to a particular embodiment, the depolymerization may be carried out in the presence of a radical initiator, advantageously a peroxide-type radical initiator. Preferably, the radical initiator is selected from the group consisting of an organic peroxide, an inorganic peroxide or superoxide such as barium peroxide ($BaO_2$), potassium superoxide ($KO_2$), cesium superoxide ($CsO_2$), a percarbonate, a peroxyhydrate compound, salts thereof, and also a mixture thereof. Depolymerization-initiating catalysts that may be mentioned include hydrogen peroxide ($H_2O_2$), azobisisobutyronitrile (AIBN), sodium (or potassium or magnesium or calcium) carbonate peroxyhydrate ($2Na_2CO_3 \cdot 3H_2O_2$), ammonium carbonate peroxyhydrate (($NH_4)_2CO_3 \cdot H_2O_2$), urea peroxide ($CO(NH_2)_2 \cdot H_2O_2$), sodium sulfate peroxyhydrate ($2Na_2SO_4 \cdot H_2O_2 \cdot 2H_2O$), complexes of $H_2O_2$ and of inorganic salts, the peroxyhydrate of poly(vinylpyrrolidone) polymer ($PVP \cdot H_2O_2$), persulfates, permanganates, perborates, and peroxyhydrates of phosphate salts.

According to another embodiment, said foam consists of poly(methyl methacrylate). The term "poly(methyl methacrylate)" refers to a polymer comprising units of the formula —[$CH_2$—$CH(CH_3)(C(O)$—O—$CH_3$)]n with n being greater than 3, preferably greater than 10, in particular greater than 50. Step c) may be carried out by thermal depolymerization, preferably at a temperature of from 200° C. to 500° C. As such a temperature the poly(methyl methacrylate) is in the solid or molten state. According to a particular embodiment, the depolymerization may be carried out in the presence of a radical initiator, advantageously a peroxide-type radical initiator. Preferably, the radical initiator is selected from the group consisting of an organic peroxide, an inorganic peroxide or superoxide such as barium peroxide ($BaO_2$), potassium superoxide ($KO_2$), cesium superoxide ($CsO_2$), a percarbonate, a peroxyhydrate compound, salts thereof, and also a mixture thereof. Depolymerization-initiating catalysts that may be mentioned include hydrogen peroxide ($H_2O_2$), azobisisobutyronitrile (AIBN), sodium (or potassium or magnesium or calcium) carbonate peroxyhydrate ($2Na_2CO_3 \cdot 3H_2O_2$), ammonium carbonate peroxyhydrate (($NH_4)_2CO_3 \cdot H_2O_2$), urea peroxide ($CO(NH_2)_2 \cdot H_2O_2$), sodium sulfate peroxyhydrate ($2Na_2SO_4 \cdot H_2O_2 \cdot 2H_2O$), complexes of $H_2O_2$ and of inorganic salts, the peroxyhydrate of poly(vinylpyrrolidone) polymer ($PVP \cdot H_2O_2$), persulfates, permanganates, perborates, and peroxyhydrates of phosphate salts.

Alternatively, when said foam consists of poly(methyl methacrylate), step c) may be carried out by dissolving the latter in an organic solvent capable of dissolving poly(methyl methacrylate). Preferably, said organic solvent is methyl methacrylate. The use of methyl methacrylate to dissolve the poly(methyl methacrylate) is advantageous since the liquid phase thus formed may be used, after an optional filtration step, in a process for the production of poly(methyl methacrylate). Alternatively, said organic solvent may be selected from the group consisting of toluene, acetone, butanone, cyclohexanone, nitroethane, chloroform, dichloromethane, benzene, chlorobenzene, xylene, methoxybenzene, diethyl phthalate, methoxypropyl acetate, ethyl acetate, ethyl lactate, formic acid.

Preferably, the dissolution of the poly(methyl methacrylate) foam is carried out at a temperature of from 20° C. to 200° C., preferably from 25° C. to 100° C., preferably 30 to 80° C. The dissolution may be carried out under pressure.

According to another embodiment, said foam consists of polyhydroxyalkanoate (i.e. PHA), preferably polypropiolactone or poly-3-hydroxypropionate. In this case, step c) is carried out by depolymerization. Preferably, the depolymerization is carried out by hydrolysis or thermally. The thermal depolymerization is carried out at a temperature of greater than 100° C., advantageously greater than 150° C., preferably greater than 200° C.; and less than 400° C., preferably less than 300° C. Preferably, the thermal depolymerization is carried out in the presence of an inert gas, such as nitrogen, $CO_2$ or argon. Preferably, the thermal depolymerization is carried out at a pressure of less than 1 bar absolute. Alternatively, the thermal depolymerization may be carried out under partial vacuum. Preferably, the thermal depolymerization is carried out in the presence of a depolymerization catalyst. Preferably, said depolymerization catalyst is selected from the group consisting of acid catalysts, such as mixed oxides, zeolites, aluminas, titanium or zirconium oxides doped with one or more of the elements P, S, W, B, Nb, Ta.

Alternatively, step c) may be carried out by hydrolysis. In this case, step c) may be carried out at a temperature of from 20° C. to 100° C. in the presence of water.

Carrying out step c) with foams of polypropiolactone type enables the formation of 3-hydroxypropionic acid, which can be subsequently upgraded into acrylic acid in a specific process.

According to another embodiment, said foam consists of polylactic acid, that is to say it contains units of the formula —[CH(CH$_3$)—C(O)O-]n with n being greater than 3, preferably greater than 10, in particular greater than 50. Step c) may be carried out by dissolution or depolymerization. The dissolution of the polylactic acid may be carried out in the presence of an organic solvent selected from tetrahydrofuran, dioxane, dioxolane, m-cresol, pyridine, N-methylpyrrolidone, butyrolactone, ethyl acetate, propylene carbonate, acetone, acetonitrile, nitrobenzene, dimethylacetamide, dichloromethane, chloroform. Alternatively, the dissolution of the polylactic acid may be carried out in the presence of an organic solvent such as a lactic acid ester. The lactic acid ester may be methyl lactate, ethyl lactate, isopropyl lactate, butyl lactate, hexyl lactate. The dissolution step may be followed by a step of filtration in order to remove any particles that are not soluble in the organic solvent.

The depolymerization of the polylactic acid may be carried out by hydrolysis at a temperature of from 80° C. to 180° C., preferably from 100° C. to 150° C., in particular from 120° C. to 140° C. The depolymerization by hydrolysis may be carried out at a pressure of less than 1 bara or at a pressure of from 1 bara to 10 bara. The depolymerization by hydrolysis may be carried out in the presence of water or of an alkaline solution of NaOH or KOH. The depolymerization by hydrolysis may optionally be carried out in the presence of a catalyst such as a Lewis acid chosen from tin octoate, tin lactate, antimony octoate, zinc octoate, APTS or triazabicyclodecene. The depolymerization by hydrolysis may optionally be carried out in the presence of a catalyst such as a Brønsted acid.

The depolymerization by hydrolysis of polylactic acid results in the formation of lactic acid, which may be upgraded via subsequent use in processes for the production of polylactic acid or else by dehydration into acrylic acid, or conversion into esters.

According to another embodiment, said foam may be a polyolefin. Preferably, the polyolefin is polyethylene or polypropylene. In this case, step c) is carried out by dissolution in an organic solvent. Step c) may be carried out at a temperature of from 100° C. to 300° C. Said organic solvent may be dimethylformamide, dimethyl sulfoxide, xylenes, tetralin, decalin or 1,2,4-trichlorobenzene. After dissolution, the liquid phase formed by the polyolefin dissolved in the organic solvent may be filtered to remove any insoluble particles. After filtration, the polyolefin dissolved in the liquid phase may be precipitated according to techniques known to those skilled in the art.

According to another embodiment, said foam may be polyimide, polycarbonate or poly(etherimide). In this case, the foam is processed by depolymerization as described above for polyurethane.

According to another embodiment, said foam may be poly(methacrylimide). In this case, the foam is processed as described above for poly(methyl methacrylate). The depolymerization of the poly(methacrylimide) makes it possible to produce methacrylonitrile, which may be upgraded in a manner equivalent to that of methyl methacrylate.

According to another embodiment, said foam may be poly(vinyl chloride) or poly(ethylene/vinyl acetate). In this case, the foam is processed as described above for a polyolefin. In the case of poly(vinyl chloride), this may be recovered by precipitation by injection of steam, which causes the evaporation of the solvent.

According to an alternative embodiment, when said foam consists of polyolefin, polystyrene or poly(vinyl chloride) or poly(ethylene/vinyl acetate), step c) may be carried out by devolatilization. Said foam is heated to a temperature such that said foam is in the molten state.

Said composition C1 contained in the pores of said foam is thus released in the gaseous state and recovered in order to be used in step d) of the present process.

During step c), the depolymerization of the dissolution of the foam will lead to the release of said composition C1 comprising at least one unsaturated fluorinated hydrocarbon. Thus, the present process comprises the step of:
  d) recovering at least a portion of said composition C1 comprising at least one unsaturated fluorinated hydrocarbon and released during step c) and optionally mixing the latter with said at least a portion of the composition recovered in step b2) to form a stream A comprising at least one unsaturated fluorinated hydrocarbon.

Said at least a portion of said composition C1 may be recovered by a suction device. Preferably, said steps c) and d) are carried out in a hermetically sealed processing chamber comprising said suction device in order to limit contamination of the gases of the composition by gases of the air. The latter comprises at least one or more suction nozzles capable of recovering at least a portion of said composition comprising at least one fluorinated hydrocarbon and released during step c). Said at least a portion of said composition C1 comprising at least one fluorinated hydrocarbon recovered in step d) may be mixed with said at least a portion of the composition C1 recovered in step b2) to form a stream A comprising at least one fluorinated hydrocarbon. Said stream A may be purified by passing through one or more dust filters. Said dust filters may have pores having a size varying between 0.5 μm and 10 μm. This purification step makes it possible to remove any particles that have been suctioned up alongside said stream A.

Said stream A formed in step d) is recovered and purified in order to separate the constituents included therein.

Thus, the present process comprises a step of:
  e) recovering and separating said stream A formed in step d) into a plurality of streams of which at least one stream B1 comprises said at least one unsaturated fluorinated hydrocarbon.

Thus, said stream A comprises said at least one unsaturated fluorinated hydrocarbon selected from the group consisting of 3,3,3-trifluoropropene, 2,3,3,3-tetrafluoropropene, (E/Z)-1,3,3,3-tetrafluoropropene, (E/Z)-1,2,3,3,3-pentafluoropropene, 2-chloro-3,3,3-trifluoropropene, 1-chloro-3,3,3-trifluoropropene, 1,1-dichloro-3,3,3-trifluoropropene and 1,2-dichloro-3,3,3-trifluoropropene, (E/Z)-1,1,1,4,4,4-hexafluorobut-2-ene, 2,4,4,4-tetrafluorobut-1-ene, and mixtures thereof.

Depending on the constituents of said composition C1, said stream A may also comprise a hydrofluorocarbon other than said at least one unsaturated fluorinated hydrocarbon, an alkane, methyl formate, an inert gas, an alcohol, an ether, a fluorinated ether, an unsaturated fluorinated ether, a ketone, a fluoroketone, a chlorofluorocarbon or water, or a mixture thereof. Preferably, said hydrofluorocarbon other than said at least one unsaturated fluorinated hydrocarbon is selected from the group consisting of difluoromethane (HFC-32), fluoroethane (HFC-161), 1,2-difluoroethane (HFC-152), 1,1-difluoroethane (HFC-152a), 1,1,2-trifluoroethane (HFC-143), 1,1,1-trifluoroethane (HFC-143a), 1,1,2,2-tetrafluoroethane (HFC-134), 1,1,1,2-tetrafluoroethane (HFC-134a), 1,1,1,2,2-pentafluoroethane (HFC-125), 1,1,1,3,3-pentafluoropropane (HFC-245fa), 1,1,1,3,3,3-hexafluoropropane (HFC-236fa), 1,1,2,3,3,3-hexafluoropropane (HFC-236ea), 1,1,1,3,3-pentafluorobutane (HFC-365mfc), 1,1,1,2,3,3,3-heptafluoropropane (HFC-227ea).

Preferably, the inert gas is nitrogen, argon or $CO_2$, or a mixture thereof.

Preferably, the chlorofluorocarbon is selected from the group consisting of trichlorofluoromethane, dichlorodifluoromethane, trichlorotrifluoroethane, dichlorotetrafluoroethane and chloropentafluoroethane.

According to a preferred embodiment, said stream A comprises 1-chloro-3,3,3-trifluoropropene and a hydrofluorocarbon other than said at least one unsaturated fluorinated hydrocarbon selected from the group consisting of difluoromethane (HFC-32), fluoroethane (HFC-161), 1,2-difluoroethane (HFC-152), 1,1-difluoroethane (HFC-152a), 1,1,2-trifluoroethane (HFC-143), 1,1,1-trifluoroethane (HFC-143a), 1,1,2,2-tetrafluoroethane (HFC-134), 1,1,1,2-tetrafluoroethane (HFC-134a), 1,1,1,2,2-pentafluoroethane (HFC-125), 1,1,1,3,3-pentafluoropropane (HFC-245fa), 1,1,1,3,3,3-hexafluoropropane (HFC-236fa), 1,1,2,3,3,3-hexafluoropropane (HFC-236ea), 1,1,1,3,3-pentafluorobutane (HFC-365mfc), 1,1,1,2,3,3,3-heptafluoropropane (HFC-227ea). Alternatively, said stream A comprises 1-chloro-3,3,3-trifluoropropene and an inert gas as described above.

Alternatively, the content of said at least one unsaturated fluorinated hydrocarbon in said stream A is between 50% and 99% by volume based on the total volume of said stream A. The content of said at least one unsaturated fluorinated hydrocarbon in said stream A may be between 51% and 99% by volume, between 52% and 99% by volume, between 53% and 99% by volume, between 54% and 99% by volume, between 55% and 99% by volume, between 56% and 99% by volume, between 57% and 99% by volume, between 58% and 99% by volume, between 59% and 99% by volume, between 60% and 99% by volume, between 61% and 99% by volume, between 62% and 99% by volume, between 63% and 99% by volume, between 64% and 99% by volume, between 65% and 99% by volume, between 66% and 99% by volume, between 67% and 99% by volume, between 68% and 99% by volume, between 69% and 99% by volume, between 70% and 99% by volume, between 71% and 99% by volume, between 72% and 99% by volume, between 73% and 99% by volume, between 74% and 99% by volume, or between 75% and 99% by volume. The content of said at least one unsaturated fluorinated hydrocarbon in said stream A may also be between 75% and 98% by volume, between 75% and 97% by volume, between 75% and 96% by volume, between 75% and 95% by volume, between 75% and 94% by volume, between 75% and 93% by volume, between 75% and 92% by volume, between 75% and 91% by volume, or between 75% and 90% by volume based on the total volume of said stream A. Said stream A, with the contents mentioned above, may be obtained when the process is carried out starting from foams M1 the pores of which contain said composition C1.

As mentioned in the present application, the present process also makes it possible to process and recycle foams containing previous generations of blowing agents, this being done simultaneously with the processing of foams M1 comprising new generation blowing agents.

Thus, in the present process, step a) may also comprise:
providing a foam M2 consisting of pores containing a composition C2 comprising a hydrofluorocarbon selected from the group consisting of difluoromethane (HFC-32), fluoroethane (HFC-161), 1,2-difluoroethane (HFC-152), 1,1-difluoroethane (HFC-152a), 1,1,2-trifluoroethane (HFC-143), 1,1,1-trifluoroethane (HFC-143a), 1,1,2,2-tetrafluoroethane (HFC-134), 1,1,1,2-tetrafluoroethane (HFC-134a), 1,1,1,2,2-pentafluoroethane (HFC-125), 1,1,1,3,3-pentafluoropropane (HFC-245fa), 1,1,1,3,3,3-hexafluoropropane (HFC-236fa), 1,1,2,3,3,3-hexafluoropropane (HFC-236ea), 1,1,1,3,3-pentafluorobutane (HFC-365mfc), 1,1,1,2,3,3,3-heptafluoropropane (HFC-227ea), or
providing a foam M3 consisting of pores containing a composition C3 comprising a chlorofluorocarbon selected from the group consisting of trichlorofluoromethane, dichlorodifluoromethane, trichlorotrifluoroethane, dichlorotetrafluoroethane, chloropentafluoroethane, or
providing a mixture of said foams M2 and M3.

When step a) provides foams M2 and/or M3 in addition to the foam M1, the foam M2 and the foam M3 consist of a polymer identical to that of said foam M1. Thus, step c) is carried out in the same manner in the presence of the foams M2 and/or M3 as for the foam M1.

Preferably, the foams M2 and M3 contain older generation blowing agents. Thus, the composition C2 and the composition C3 are devoid of unsaturated fluorinated hydrocarbon as defined in the present application (representing the new generation of blowing agents).

Preferably, the composition C2 and the composition C3 are devoid of unsaturated fluorinated hydrocarbon comprising one carbon-carbon double bond; in particular, the composition C2 and the composition C3 are devoid of unsaturated fluorinated hydrocarbon comprising three or four carbon atoms and one carbon-carbon double bond. More particularly, the composition C2 and the composition C3 are devoid of unsaturated fluorinated hydrocarbon selected from the group consisting of 3,3,3-trifluoropropene, 2,3,3,3-tetrafluoropropene, (E/Z)-1,3,3,3-tetrafluoropropene, (E/Z)-1,2,3,3,3-pentafluoropropene, 2-chloro-3,3,3-trifluoropropene, 1-chloro-3,3,3-trifluoropropene, 1,1-dichloro-3,3,3-trifluoropropene and 1,2-dichloro-3,3,3-trifluoropropene, (E/Z)-1,1,1,4,4,4-hexafluorobut-2-ene, 2,4,4,4-tetrafluorobut-1-ene, and mixtures thereof. Favorably, the composition C2 and the composition C3 are devoid of 1-chloro-3,3,3-trifluoropropene.

When foams M2 and/or M3 have been provided in step a), the process comprises the following steps b) to e):
b1) optionally grinding or compressing said foam M1, said foam M2 and/or said foam M3 provided in step a) to form a ground foam or a compressed foam;
b2) optionally recovering at least a portion of said composition C1 and at least a portion of said composition C2 and/or at least a portion of said composition C3, released during step b1);
c) depolymerizing or dissolving said foam M1 and said foam M2 and/or said foam M3 provided in step a) or said ground or compressed foam obtained in step b1);
d) recovering at least a portion of said composition C1 and at least a portion of said composition C2 and/or at least a portion of said composition C3, released during step c), and optionally mixing them with those recovered in step b2) to form a stream A;
e) recovering and separating said stream A into a plurality of streams of which at least one stream B1 comprises said at least one unsaturated fluorinated hydrocarbon.

Thus, according to a particular embodiment, the present process comprises the steps of:
a) providing a foam M1 consisting of pores containing a composition C1 comprising at least one unsaturated fluorinated hydrocarbon; and
providing a foam M2 consisting of pores containing a composition C2 comprising a hydrofluorocarbon selected from the group consisting of difluoromethane (HFC-32), fluoroethane (HFC-161), 1,2-difluoroethane (HFC-152), 1,1-difluoroethane (HFC-152a), 1,1,2-trifluoroethane (HFC-143), 1,1,1-trifluoroethane (HFC-143a), 1,1,2,2-tetrafluoroethane (HFC-134), 1,1,1,2-tetrafluoroethane (HFC-134a), 1,1,1,2,2-pentafluoroethane (HFC-125), 1,1,1,3,3-pentafluoropropane (HFC-245fa), 1,1,1,3,3,3-hexafluoropropane (HFC-236fa), 1,1,2,3,3,3-hexafluoropropane (HFC-236ea), 1,1,1,3,3-pentafluorobutane (HFC-365mfc), 1,1,1,2,3,3,3-heptafluoropropane (HFC-227ea), or
providing a foam M3 consisting of pores containing a composition C3 comprising a chlorofluorocarbon selected from the group consisting of trichlorofluoromethane, dichlorodifluoromethane, trichlorotrifluoroethane, dichlorotetrafluoroethane, chloropentafluoroethane, or
providing a mixture of said foams M2 and M3;
b1) optionally grinding or compressing said foam M1, said foam M2 and/or said foam M3 provided in step a) to form a ground foam or a compressed foam;
b2) optionally recovering at least a portion of said composition C1 and at least a portion of said composition C2 and/or at least a portion of said composition C3, released during step b1);
c) depolymerizing or dissolving said foam M1 and said foam M2 and/or said foam M3 provided in step a) or said ground or compressed foam obtained in step b1);
d) recovering at least a portion of said composition C1 and at least a portion of said composition C2 and/or at least a portion of said composition C3, released during step c), and optionally mixing them with those recovered in step b2) to form a stream A;
e) recovering and separating said stream A into a plurality of streams of which at least one stream B1 comprises said at least one unsaturated fluorinated hydrocarbon.

In this embodiment, preferably, said stream A comprises a content of said at least one fluorinated hydrocarbon of between 0.1% and 50% by volume based on the total volume of said stream A. In particular, the content of said at least one unsaturated fluorinated hydrocarbon in said stream A is between 0.1% and 50% by volume based on the total volume of said stream A.

The content of said at least one unsaturated fluorinated hydrocarbon in said stream A may be between 0.5% and 50% by volume, between 1% and 50% by volume, between 2% and 50% by volume, between 3% and 50% by volume, between 4% and 50% by volume, between 5% and 50% by volume, between 6% and 50% by volume, between 7% and 50% by volume, between 8% and 50% by volume, between 9% and 50% by volume, between 10% and 50% by volume, between 11% and 50% by volume, between 12% and 50% by volume, between 13% and 50% by volume, between 14% and 50% by volume, between 15% and 50% by volume, between 16% and 50% by volume, between 17% and 50% by volume, between 18% and 50% by volume, between 19% and 50% by volume, between 20% and 50% by volume, between 21% and 50% by volume, between 22% and 50% by volume, between 23% and 50% by volume, between 24% and 50% by volume, or between 25% and 50% by volume. The content of said at least one unsaturated fluorinated hydrocarbon in said stream A may also be between 0.1% and 49% by volume, between 0.1% and 48% by volume, between 0.1% and 47% by volume, between 0.1% and 46% by volume, between 0.1% and 45% by volume, between 0.1% and 44% by volume, between 0.1% and 43% by volume, between 0.1% and 42% by volume, between 0.1% and 41% by volume, between 0.1% and 40% by volume, between 0.1% and 39% by volume, between 0.1% and 38% by volume, between 0.1% and 37% by volume, between 0.1% and 36% by volume, between 0.1% and 35% by volume, between 0.1% and 34% by volume, between 0.1% and 33% by volume, between 0.1% and 32% by volume, between 0.1% and 31% by volume, between 0.1% and 30% by volume, between 0.1% and 29% by volume, between 0.1% and 28% by volume, between 0.1% and 27% by volume, between 0.1% and 26% by volume, between 0.1% and 25% by volume, between 0.1% and 24% by volume, between 0.1% and 23% by volume, between 0.1% and 22% by volume, between 0.1% and 21% by volume, or between 0.1% and 20% by volume based on the total volume of said stream A. Said stream A, with the contents mentioned above, may be obtained when the process is carried out starting from a mixture of foams, a portion of the foams containing compounds other than said unsaturated fluorinated hydrocarbon, for example said hydrofluorocarbon other than said at least one unsaturated fluorinated hydrocarbon as defined in the present invention, or a chlorofluorocarbon.

Said stream A is preferably separated by distillation, azeotropic distillation, pressurized distillation, extractive distillation, cold separation, absorption in a solvent, or a combination thereof. The separation of said stream A by any one of the techniques above results in the formation of a plurality of streams B of which at least one stream B1 comprises said unsaturated fluorinated hydrocarbon, preferably comprising 1-chloro-3,3,3-trifluoropropene (i.e. HCFO-1233zd).

In this stream B1, the molar content of said at least one unsaturated fluorinated hydrocarbon, preferably of HCFO-1233zd, is greater than the molar content of said at least one unsaturated fluorinated hydrocarbon, preferably of HCFO-1233zd, in said stream A. The temperature and pressure conditions applied for these distillations are such that the molar content of at least one said unsaturated fluorinated hydrocarbon, preferably of HCFO-1233zd, in said stream B1 is greater than 80%, advantageously greater than 85%, preferably greater than 90%, in particular greater than 95%.

The step of separation by distillation preferably comprises at least two distillation columns. The first distillation column makes it possible for example to remove a portion of the products having a boiling point lower than that of said at least one unsaturated fluorinated hydrocarbon, preferably lower than that of 1-chloro-3,3,3-trifluoropropene (HCFO-1233zd). The second distillation column makes it possible for example to remove a portion of the products having a boiling point greater than that of said at least one unsaturated fluorinated hydrocarbon, preferably greater than that of 1-chloro-3,3,3-trifluoropropene. Alternatively, the first distillation column makes it possible for example to remove a portion of the products having a boiling point greater than that of said at least one unsaturated fluorinated hydrocarbon, preferably greater than that of 1-chloro-3,3,3-trifluoropropene (HCFO-1233zd). The second distillation column makes it possible for example to remove a portion of the products having a boiling point lower than that of said at least one unsaturated fluorinated hydrocarbon, preferably lower than that of 1-chloro-3,3,3-trifluoropropene.

Said flow B1 is that obtained after said at least second distillation.

As indicated above, a plurality of streams is obtained in step e). Besides the stream B1, a stream B2 comprising all or some of the composition C2 and/or C3 may also be obtained. The compounds contained in the composition C2 and/or C3 and recovered in the stream B2 may be upgraded and used as synthesis precursor or intermediate for the production of pharmaceutical compounds, phytosanitary compounds, fluorinated polymers or for the production of other fluorinated gases having applications in refrigeration, heat transfer fluids or blowing agents (for example HFC-152a or HFC-143a may be used for the preparation of 1,1-difluoroethylene).

As mentioned above, extractive distillation may be used to separate the constituents present in said stream A. In this case, said stream A is mixed with an organic extraction agent and the resulting mixture is distilled to form said stream B1 comprising said at least one fluorinated hydrocarbon.

Extractive distillation is particularly advantageous for separating said fluorinated hydrocarbon from said hydrofluorocarbon other than said at least one fluorinated hydrocarbon. Thus, said stream A comprising at least one fluorinated hydrocarbon and said hydrofluorocarbon other than said at least one fluorinated hydrocarbon is mixed with said organic extraction agent. The resulting mixture is distilled to form said stream B1 comprising said at least one fluorinated hydrocarbon and a stream B2 comprising said organic extraction agent and said hydrofluorocarbon other than said at least one fluorinated hydrocarbon.

Preferably, said organic extraction agent has a boiling point of between 10° C. and 200° C.

According to a preferred embodiment, said organic extraction agent has a separation factor $S_{1,2}$ of greater than or equal to 1.1, said separation factor being calculated by the formula $S_{1,2}=(\gamma_{1,S}*P1)/(\gamma_{2,S}*P2)$ in which $\gamma_{1,S}$ represents the activity coefficient of said at least one fluorinated hydrocarbon in said organic extraction agent at infinite dilution, P1 represents the saturation vapor pressure of said at least one fluorinated hydrocarbon, $\gamma_{2,S}$ represents the activity coefficient of said hydrofluorocarbon other than said at least one fluorinated hydrocarbon and selected from the group consisting of difluoromethane (HFC-32), fluoroethane (HFC-161), 1,2-difluoroethane (HFC-152), 1,1-difluoroethane (HFC-152a), 1,1,2-trifluoroethane (HFC-143), 1,1,1-trifluoroethane (HFC-143a), 1,1,2,2-tetrafluoroethane (HFC-134), 1,1,1,2-tetrafluoroethane (HFC-134a), 1,1,1,2,2-pentafluoroethane (HFC-125), 1,1,1,3,3-pentafluoropropane (HFC-245fa), 1,1,1,3,3,3-hexafluoropropane (HFC-236fa), 1,2,3,3,3-hexafluoropropane (HFC-236ea), 1,1,1,3,3-pentafluorobutane (HFC-365mfc), 1,1,1,2,3,3,3-heptafluoropropane (HFC-227ea) in said organic extraction agent at infinite dilution, P2 represents the saturation vapor pressure of said hydrofluorocarbon other than said at least one fluorinated hydrocarbon and selected from the group consisting of difluoromethane (HFC-32), fluoroethane (HFC-161), 1,2-difluoroethane (HFC-152), 1,1-difluoroethane (HFC-152a), 1,1,2-trifluoroethane (HFC-143), 1,1,1-trifluoroethane (HFC-143a), 1,1,2,2-tetrafluoroethane (HFC-134), 1,1,1,2-tetrafluoroethane (HFC-134a), 1,1,1,2,2-pentafluoroethane (HFC-125), 1,1,1,3,3-pentafluoropropane (HFC-245fa), 1,1,1,3,3,3-hexafluoropropane (HFC-236fa), 1,1,2,3,3,3-hexafluoropropane (HFC-236ea), 1,1,1,3,3-pentafluorobutane (HFC-365mfc), 1,1,1,2,3,3,3-heptafluoropropane (HFC-227ea); advantageously the separation factor $S_{1,2}$ may be greater than or equal to 1.2, preferably greater than or equal to 1.4, more preferentially greater than or equal to 1.5, in particular greater than or equal to 1.8, more particularly greater than or equal to 1.9.

According to a preferred embodiment, said organic extraction agent has a separation factor $S_{1,2}$ of greater than or equal to 1.1, said separation factor being calculated by the formula $S_{1,2}=(\gamma_{1,S}*P1)/(\gamma_{2,S}*P2)$ in which $\gamma_{1,S}$ represents the activity coefficient of one of the fluorinated hydrocarbons selected from the group consisting of 3,3,3-trifluoropropene, 2,3,3,3-tetrafluoropropene, (E/Z)-1,3,3,3-tetrafluoropropene, (E/Z)-1,2,3,3,3-pentafluoropropene, 2-chloro-3,3,3-trifluoropropene, 1-chloro-3,3,3-trifluoropropene, 1,1-dichloro-3,3,3-trifluoropropene and 1,2-dichloro-3,3,3-trifluoropropene, (E/Z)-1,1,1,4,4,4-hexafluorobut-2-ene, 2,4,4,4-tetrafluorobut-1-ene in said organic extraction agent at infinite dilution, P1 represents the saturation vapor pressure of one of the fluorinated hydrocarbons selected from the group consisting of 3,3,3-trifluoropropene, 2,3,3,3-tetrafluoropropene, (E/Z)-1,3,3,3-tetrafluoropropene, (E/Z)-1,2,3,3-pentafluoropropene, 2-chloro-3,3,3-trifluoropropene, 1-chloro-3,3,3-trifluoropropene, 1,1-dichloro-3,3,3-trifluoropropene and 1,2-dichloro-3,3,3-trifluoropropene, (E/Z)-1,1,1,4,4,4-hexafluorobut-2-ene, 2,4,4,4-tetrafluorobut-1-ene, $\gamma_{2,S}$ represents the activity coefficient of said hydrofluorocarbon other than said at least one fluorinated hydrocarbon and selected from the group consisting of difluoromethane (HFC-32), fluoroethane (HFC-161), 1,2-difluoroethane (HFC-152), 1,1-difluoroethane (HFC-152a), 1,1,2-trifluoroethane (HFC-143), 1,1,1-trifluoroethane (HFC-143a), 1,1,2,2-tetrafluoroethane (HFC-134), 1,1,1,2-tetrafluoroethane (HFC-134a), 1,1,1,2,2-pentafluoroethane (HFC-125), 1,1,1,3,3-pentafluoropropane (HFC-245fa), 1,1,1,3,3,3-hexafluoropropane (HFC-236fa), 1,1,2,3,3,3-hexafluoropropane (HFC-236ea), 1,1,1,3,3-pentafluorobutane (HFC-365mfc), 1,1,1,2,3,3,3-heptafluoropropane (HFC-227ea) in said organic extraction agent at infinite dilution, P2 represents the saturation vapor pressure of said hydrofluorocarbon other than said at least one fluorinated hydrocarbon and selected from the group consisting of difluoromethane (HFC-32), fluoroethane (HFC-161), 1,2-difluoroethane (HFC-152), 1,1-difluoroethane (HFC-152a), 1,1,2-trifluoroethane (HFC-143), 1,1,1-trifluoroethane (HFC-143a), 1,1,2,2-tetrafluoroethane (HFC-134), 1,1,1,2-tetrafluoroethane (HFC-134a), 1,1,1,2,2-pentafluoroethane (HFC-125), 1,1,1,3,3-pentafluoropropane (HFC-245fa), 1,1,1,3,3,3-hexafluoropropane (HFC-236fa), 1,1,2,3,3,3-hexafluoropropane (HFC-236ea), 1,1,1,3,3-pentafluorobutane (HFC-365mfc), 1,1,1,2,3,3,3-heptafluoropropane (HFC-227ea); advantageously the separation factor $S_{1,2}$ may be greater than or equal to 1.2, preferably greater than or equal to 1.4, more preferentially greater than or equal to 1.5, in particular greater than or equal to 1.8, more particularly greater than or equal to 1.9.

The same compound must be considered for the values of $\gamma_{1,S}$ and of P1. Thus, if the activity coefficient taken into account for $\gamma_{1,S}$ is that of 3,3,3-trifluoropropene, P1 represents the saturation vapor pressure of 3,3,3-trifluoropropene. The same compound must be considered for the values of $\gamma_{2,S}$ and of P2. Thus, if $\gamma_{2,S}$ represents the activity coefficient of difluoromethane, then P2 represents the saturation vapor pressure of difluoromethane.

According to a preferred embodiment, said organic extraction agent has a separation factor $S_{1,2}$ of greater than or equal to 1.1, said separation factor being calculated by the formula $S_{1,2}=(\gamma_{1,S}*P1)/(\gamma_{2,S}*P2)$ in which $\gamma_{1,S}$ represents the activity coefficient of 1-chloro-3,3,3-trifluoropropene in said organic extraction agent at infinite dilution, P1 represents the saturation vapor pressure of 1-chloro-3,3,3-trifluoropropene, $\gamma_{2,S}$ represents the activity coefficient of said hydrofluorocarbon other than said at least one fluorinated hydrocarbon and selected from the group consisting of difluoromethane (HFC-32), fluoroethane (HFC-161), 1,2-difluoroethane (HFC-152), 1,1-difluoroethane (HFC-152a), 1,1,2-trifluoroethane (HFC-143), 1,1,1-trifluoroethane (HFC-143a), 1,1,2,2-tetrafluoroethane (HFC-134), 1,1,1,2-tetrafluoroethane (HFC-134a), 1,1,1,2,2-pentafluoroethane (HFC-125), 1,1,1,3,3-pentafluoropropane (HFC-245fa), 1,1,1,3,3,3-hexafluoropropane (HFC-236fa), 1,1,2,3,3,3-hexafluoropropane (HFC-236ea), 1,1,1,3,3-pentafluorobutane (HFC-365mfc), 1,1,1,2,3,3,3-heptafluoropropane (HFC-227ea) in said organic extraction agent at infinite dilution, P2 represents the saturation vapor pressure of said hydrofluorocarbon other than said at least one fluorinated hydrocarbon and selected from the group consisting of difluoromethane (HFC-32), fluoroethane (HFC-161), 1,2-difluoroethane (HFC-152), 1,1-difluoroethane (HFC-152a), 1,1,2-trifluoroethane (HFC-143), 1,1,1-trifluoroethane (HFC-143a), 1,1,2,2-tetrafluoroethane (HFC-134), 1,1,1,2-tetrafluoroethane (HFC-134a), 1,1,1,2,2-pentafluoroethane (HFC-125), 1,1,1,3,3-pentafluoropropane (HFC-245fa), 1,1,1,3,3,3-hexafluoropropane (HFC-236fa), 1,1,2,3,3,3-hexafluoropropane (HFC-236ea), 1,1,1,3,3-pentafluorobutane (HFC-365mfc), 1,1,1,2,3,3,3-heptafluoropropane (HFC-227ea); advantageously the separation factor $S_{1,2}$ may be greater than or equal to 1.2, preferably greater than or equal to 1.4, more preferentially greater than or equal to 1.5, in particular greater than or equal to 1.8, more particularly greater than or equal to 1.9.

In the present application, the saturation vapor pressure is considered for a temperature of 25° C.

According to a preferred embodiment, said organic extraction agent has an absorption capacity $C_{2,S}$ of greater than or equal to 0.20, said absorption capacity being calculated by the formula $C_{2,S}=1/(\gamma_{2,S})$ in which $\gamma_{2,S}$ represents the activity coefficient of said hydrofluorocarbon other than said at least one fluorinated hydrocarbon and selected from the group consisting of difluoromethane (HFC-32), fluoroethane (HFC-161), 1,2-difluoroethane (HFC-152), 1,1-difluoroethane (HFC-152a), 1,1,2-trifluoroethane (HFC-143), 1,1,1-trifluoroethane (HFC-143a), 1,1,2,2-tetrafluoroethane (HFC-134), 1,1,1,2-tetrafluoroethane (HFC-134a), 1,1,1,2,2-pentafluoroethane (HFC-125), 1,1,1,3,3-pentafluoropropane (HFC-245fa), 1,1,1,3,3,3-hexafluoropropane (HFC-236fa), 1,1,2,3,3,3-hexafluoropropane (HFC-236ea), 1,1,1,3,3-pentafluorobutane (HFC-365mfc), 1,1,1,2,3,3,3-heptafluoropropane (HFC-227ea) in said organic extraction agent at infinite dilution; advantageously, the absorption capacity $C_{2,S}$ is greater than or equal to 0.40, preferably greater than or equal to 0.60, more preferentially greater than or equal to 0.80, in particular greater than or equal to 0.90, more particularly greater than or equal to 1.0, favorably greater than or equal to 1.05.

According to a preferred embodiment, said organic extraction agent is a solvent chosen from the group consisting of hydrocarbon, halohydrocarbon, alcohol, ketone, amine, ester, ether, aldehyde, nitrile, carbonate, thioalkyl, amide and heterocycle. Advantageously, said organic extraction agent is a solvent selected from the group consisting of alcohol, ketone, amine, ester and heterocycle.

In the context of extractive distillation, the term "hydrocarbon" as used herein refers to linear or branched $C_1$-$C_{20}$ alkane, $C_3$-$C_{20}$ cycloalkane, $C_5$-$C_{20}$ alkene, $C_5$-$C_{20}$ cycloalkene, or $C_6$-$C_{18}$ arene compounds. For example, the term "alkane" refers to compounds of formula $C_nH_{2n+2}$ in which n is between 1 and 20. The term "$C_1$-$C_{20}$ alkane" includes, for example, pentane, hexane, heptane, octane, nonane and decane, or isomers thereof. The term "$C_5$-$C_{20}$ alkene" refers to hydrocarbon-based compounds comprising one or more carbon-carbon double bonds and comprising from 5 to 20 carbon atoms. The term "$C_3$-$C_{20}$ cycloalkane" refers to a saturated hydrocarbon-based ring comprising from 3 to 20 carbon atoms. The term "$C_6$-$C_{18}$ aryl" refers to cyclic and aromatic hydrocarbon-based compounds comprising from 6 to 18 carbon atoms. The term "$C_5$-$C_{20}$ cycloalkene" refers to cyclic hydrocarbon-based compounds comprising from 5 to 20 carbon atoms and comprising one or more carbon-carbon double bonds. The term "alkyl" denotes a monovalent radical resulting from a linear or branched alkane comprising from 1 to 20 carbon atoms. The term "cycloalkyl" denotes a monovalent radical resulting from a cycloalkane comprising from 3 to 20 carbon atoms. The term "aryl" denotes a monovalent radical resulting from an arene comprising from 6 to 18 carbon atoms. The term "alkenyl" denotes a monovalent radical of 2 to 20 carbon atoms and at least one carbon-carbon double bond. The term "alkynyl" denotes a monovalent radical of 2 to 20 carbon atoms and at least one carbon-carbon triple bond. The term "halogen" refers to an —F, —Cl, —Br or —I group. The term "cycloalkenyl" refers to a monovalent radical resulting from a cycloalkene comprising from 3 to 20 carbon atoms. The $C_1$-$C_{20}$ alkyl, $C_2$-$C_{20}$ alkenyl, $C_2$-$C_{20}$ alkynyl, $C_3$-$C_{20}$ cycloalkyl, $C_3$-$C_{20}$ cycloalkenyl, and $C_6$-$C_{18}$ aryl substituents may be unsubstituted or substituted by one or more —OH, halogen, —NR$^a$C(O)R$^b$, —C(O)NR$^a$R$^b$—CN, —NO$_2$, —NR$^a$R$^b$, —OR$^a$, —SR$^a$, —CO$_2$R$^a$, —OC(O)OR$^a$, —OC(O)R$^a$, —C(O)H, or —C(O)R$^a$ substituents, in which R$^a$ and R$^b$ are each independently hydrogen, unsubstituted $C_1$-$C_{20}$ alkyl, unsubstituted $C_2$-$C_{20}$ alkenyl, unsubstituted $C_2$-$C_{20}$ alkynyl, unsubstituted $C_3$-$C_{20}$ cycloalkyl, unsubstituted $C_3$-$C_{20}$ cycloalkenyl, or unsubstituted $C_6$-$C_{18}$ aryl. In the —NR$^a$R$^b$ substituents, R$^a$ and R$^b$ can form, with the nitrogen atom to which they are attached, a saturated or unsaturated, aromatic or non-aromatic, 5- to 10-membered heterocycle.

The term "halohydrocarbons" refers to compounds of formula R$^a$X in which R$^a$ is chosen from $C_1$-$C_{20}$ alkyl, $C_2$-$C_{20}$ alkenyl, $C_2$-$C_{20}$ alkynyl, $C_3$-$C_{20}$ cycloalkyl, $C_3$-$C_{20}$ cycloalkenyl and $C_6$-$C_{18}$ aryl and X represents a chlorine, fluorine, bromine or iodine atom. The $C_1$-$C_{20}$ alkyl, $C_2$-$C_{20}$ alkenyl, $C_2$-$C_{20}$ alkynyl, $C_3$-$C_{20}$ cycloalkyl, $C_3$-$C_{20}$ cycloalkenyl and $C_6$-$C_{18}$ aryl substituents may be unsubstituted or substituted by one or more —OH, halogen, —$NR^aC(O)R^b$, —$C(O)NR^aR^b$—CN, —$NO_2$, —$NR^aR^b$, —$OR^a$, —$SR^a$, —$CO_2R^a$, —$OC(O)OR^a$, —$OC(O)R^a$, —$C(O)H$, —$C(O)R^a$ substituents in which $R^a$ and $R^b$ are as defined above.

The term "alcohol" refers to hydrocarbons or halohydrocarbons as defined above in which at least one hydrogen atom is replaced with a hydroxyl group —OH.

The term "ketone" refers to hydrocarbons comprising at least one or more carbonyl functional groups $R^c$—$C(O)$—$R^d$ in which $R^c$ and $R^d$ are each independently a $C_1$-$C_{20}$ alkyl, $C_2$-$C_{20}$ alkenyl, $C_2$-$C_{20}$ alkynyl, $C_3$-$C_{20}$ cycloalkyl, $C_3$-$C_{20}$ cycloalkenyl or $C_6$-$C_{18}$ aryl and may be unsubstituted or substituted by one or more —OH, halogen, —$NR^aC(O)R^b$, —$C(O)NR^aR^b$—CN, —$NO_2$, —$NR^aR^b$, —$OR^a$, —$SR^a$, —$CO_2R^a$, —$OC(O)OR^a$, —$OC(O)R^a$, —$C(O)H$, —$C(O)R^a$ substituents in which $R^a$ and $R^b$ are as defined above, $R^c$ and $R^d$ possibly being linked together to form, with the carbonyl group to which they are attached, a 4- to 10-membered and preferably 4- to 7-membered cyclic ketone. The cyclic ketone may also comprise one or more carbon-carbon double bonds. The cyclic ketone may also be unsubstituted or substituted by one or more substituents as defined above.

The term "amine" refers to hydrocarbons comprising at least one or more amine functional groups —$NR^cR^d$ in which $R^c$ and $R^d$ are as defined above, $R^c$ and $R^d$ possibly being linked together to form, with the nitrogen atom to which they are attached, a 4- to 10-membered aromatic or non-aromatic heterocycle.

The term "esters" refers to compounds of formula $R^c$—$C(O)$—$O$—$R^d$ in which $R^c$ and $R^d$ are as defined above, $R^c$ and $R^d$ possibly being linked together to form, with the ester group, a ring comprising from 4 to 20 carbon atoms.

The term "ether" refers to compounds of formula $R^c$—$O$—$R^d$ in which $R^c$ and $R^d$ are as defined above, $R^c$ and $R^d$ possibly being linked together to form, with the oxygen atom to which they are attached, a heterocycle comprising from 4 to 20 carbon atoms.

The term "aldehyde" refers to compounds comprising at least one or more —$C(O)$—H functional groups.

The term "nitrile" refers to compounds comprising at least one or more —CN functional groups.

The term "carbonate" refers to compounds of formula $R^c$—$O$—$C(O)$—$O$—$R^d$ in which $R^c$ and $R^d$ are as defined above.

The term "thioalkyl" refers to compounds of formula $R^cSR^d$ in which $R^c$ and $R^d$ are as defined above.

The term "amide" relates to compounds of formula $R^cC(O)NR^eR^d$ in which $R^c$ and $R^d$ are as defined above, $R^e$ having the same definition as $R^a$, $R^c$ and $R^d$; possibly being linked together to form, with the amide group —C(O)N— to which they are attached, a 4- to 10-membered and preferably 4- to 7-membered cyclic amide. The cyclic amide may also comprise one or more carbon-carbon double bonds. The cyclic amide may also be unsubstituted or substituted by one or more substituents as defined above.

The term "heterocycle" denotes a 4- to 10-membered carbon-based ring, at least one of the ring members of which is a heteroatom selected from the group consisting of O, S, P and N. The heterocycle may comprise one or more carbon-carbon double bonds or one or more carbon-heteroatom double bonds or one or more heteroatom-heteroatom double bonds. Preferably, the heterocycle may comprise 1, 2, 3, 4 or 5 heteroatoms as defined above. In particular, the heterocycle may comprise 1, 2 or 3 heteroatoms selected from oxygen, nitrogen and sulfur. Preferably, the heterocycle may be a 4- to 6-membered carbon-based ring, 1, 2 or 3 ring members of which are heteroatoms selected from O and N. The heterocycle may be unsubstituted or substituted by one or more substituents chosen from —OH, halogen, —$NR^aC(O)R^b$, —$C(O)NR^aR^b$—CN, —$NO_2$, —$NR^aR^b$, —$OR^a$, —$SR^a$, —$CO_2R^a$, —$OC(O)OR^a$, —$OC(O)R^a$, —$C(O)H$ and —$C(O)R^a$ in which $R^a$ and $R^b$ are as defined above.

Preferably, the hydrocarbons are selected from the group consisting of cyclohexene, 1,3,5-triethylbenzene, 2,4,4-trimethyl-1-pentene, 1-methylcyclohexene, 1,4-dimethylbenzene, styrene, 1,3,5-trimethylbenzene, 1,2,4,5-tetramethylbenzene and 1,3-diethenylbenzene.

Preferably, the halohydrocarbons are selected from the group consisting of iodomethane, bromoethane, chlorobromomethane, iodoethane, 2-bromopropane, dichlorobromomethane, 2-chloropropane, 2-iodopropane, bromotrichloromethane, trichloroacetaldehyde, 1,2-dibromopropane, 2-bromobutane, 1,2-dichloropropane, 1,1,2-trichloroethane, 1,2,3-trichloropropene, 1,2-dibromoethane, 1-bromopropane, 3-bromopropene, 1-bromo-2-chloroethane, 1,2-dichloroethane, 1-iodopropane, 2-bromopentane, 1-bromo-3-methylbutane, tribromomethane, 1-bromobutane, 1-chloro-3-bromopropane, 1-bromopentane, 1,3-dichloropropane, 1-bromo-3-fluoropropane, 1,2-dibromo-1-fluoroethane, 1-bromo-1,2-difluoroethylene, bromofluoromethane, 1,1,1-trifluoro-2-bromoethane, 1-chloro-3-fluoropropane, 1-chloro-4-fluorobutane, 2-bromo-2-methylpropane, 2-chloro-2-methylpropane, 2-bromo-2-methylbutane, 2,3-dichloro-2-methylbutane, 1-iodobutane, 1,1,2-trichloropropane, 1,3-dichlorobutane, 2,3-dichlorobutane, 1,2,2-trichloropropane, cis-1,3-dichloropropene, trans-1,3-dichloropropene, 1,3-dichloro-trans-2-butene, 1,2-dichloro-2-butene and 2-chloro-2-methylbutane.

Preferably, the alcohols are selected from the group consisting of methanol, ethanol, 2-propanol, 2,2-dimethyl-1-propanol, 2,2,2-trifluoroethanol, tert-butanol, 2,2,3,3-tetrafluoro-1-propanol, 2-chloro-1-propanol, propanol, 2-allyloxyethanol, 2-butanol, 2-aminophenol, 2-methyl-2-butanol, 2-ethyl-1-butanol, isobutanol, 3-pentanol, 1-butanol, 1-methoxy-2-propanol, 1-(dimethylamino)-2-propanol, 2-methyl-1-pentanol, 3-methyl-3-pentanol, 2-methoxy-1-propanol, 1-ethoxy-2-propanol, 4-methyl-2-pentanol, 2-chloroethanol, 1,2-octanediol, 2-(dimethylamino)ethanol, 3-hexanol, 2-hexanol, 2-ethoxy-1-propanol, 1-pentanol, 2-propoxyethanol, 1-propoxy-2-propanol, 2,2-difluoroethanol, 1,1,1-trifluoro-2-propanol, 4,4,4-trifluorobutanol, 3-fluoropropanol, 2,3-dimethylbutanol and 1-chloro-2-methyl-2-propanol.

Preferably, the ketones are selected from the group consisting of propanone, butanone, 3-pentanone, 2-pentanone, 3,3-dimethyl-2-butanone, 4-methyl-2-pentanone, 2-hexanone, 5-hexen-2-one, 4-methyl-2-hexanone, and 1,1,1-trifluoro-2-propanone.

Preferably, the amines are selected from the group consisting of ethylamine, isopropylamine, ethylmethylamine, 2-amino-2-methylpropane, N-propylamine, isopropylmethylamine, diethylamine, 2-butanamine, N-methylpropylamine, 1-butylamine, diisopropylamine, 3-methyl-2-butanamine, 3-pentylamine, N-methylbutylamine, 1-methoxy-2-propanamine, 2-methoxyethanamine, 2-methoxy-1-propanamine, N-pentylamine, N-methylhydroxylamine, dipropylamine, 2-ethoxyethanamine, N-methyl-1,2-ethanediamine, pyridine, 1,2-diaminoethane, 1,2-propanediamine, 2-ethylbutylamine, N-ethylethylenediamine, 2-methylpyridine, 4-methyl-2-hexanamine, hexylamine, cyclohexylamine, N-ethyl-2-dimethylaminoethylamine, 1,3-propanediamine, 2-heptanamine, N,N-diethylethylenediamine, 2,6-dimethylpyridine, 4-methylpyridine, NN-diethyl-1,2-ethanediamine, dimethylethanolamine and 1,1-diethoxy-N,N-dimethylmethanamine.

Preferably, the esters are selected from the group consisting of methyl acetate, ethyl acetate, N-propyl formate, isopropyl acetate, tert-butyl acetate, ethyl propionate, sec-butyl acetate, diethyl carbonate, N-butyl acetate, bromoacetic acid methyl ester, methyl formate, methyl hexanoate and isopropyl formate.

Preferably, the ethers are selected from the group consisting of diethyl ether, 2-ethoxypropane, methyl t-butyl ether, 2,2-dimethoxypropane, 1-ethoxy-2-methylpropane, 1,2-dimethoxyethane, diethoxymethane, 1-ethoxybutane, 1-methoxypentane, 1,2-dimethoxypropane, 1,1-diethoxyethane, trimethoxymethane, 2-chloro-1,1-dimethoxyethane, 2,2-diethoxypropane, 1,1-diethoxypropane, 2-methoxyethanol, methoxycyclohexane, chloromethoxymethane, ethoxyethanol, di-N-butyl ether, diisopropyl ether, 1-ethoxyhexane, 1,1,1-triethoxyethane, 1-methoxy-2-acetoxypropane, dimethoxymethane, ethoxyethene, di-N-propyl ether, 2-methoxy-1-propene, 2,2,2-trifluoroethyl methyl ether, methyl cyclopropyl ether, 2-ethoxy-2-methylpropane, 2-methoxybutane, sec-butyl tert-butyl ether, isobutyl tert-butyl ether, 1-methoxy-2-methylbutane and isopropyl isobutyl ether.

Preferably, the aldehydes are selected from the group consisting of acetaldehyde, isobutanal, methylglyoxal, 2-methylbutanal, 2,6-dimethyl-5-heptenal, hexanal and ethanedial.

Preferably, the nitriles are selected from the group consisting of acetonitrile, propionitrile, butyronitrile, valeronitrile and (methyleneamino)acetonitrile.

Preferably, the carbonate is diethyl carbonate.

Preferably, the amides include ethanethioamide.

Preferably, the thioalkyls are selected from the group consisting of ethanethiol, dimethyl sulfide, 2-propanethiol, tert-butylthiol, 3-mercapto-1,2-propanediol, 1-propanethiol, butanethiol, tetrahydrothiophene, 1-pentanethiol, diethyl sulfide, 2-butanethiol, 2-methyl-1-propanethiol and 4-methoxy-2-methyl-2-butanethiol.

Preferably, the heterocycles are selected from the group consisting of N-ethylmorpholine, 1-methylpiperazine, N-methylmorpholine, 2-methylpyrazine, tetrahydrofuran, 1,3,5-trioxane, dioxane, 1,3-dioxane, piperidine and 2,6-dimethylmorpholine. Dioxane refers to 1,4-dioxane. The present process may also comprise a step of bringing said stream A or said stream B1 into contact with an adsorbent. Said adsorbent may be a zeolite or a molecular sieve having a pore opening of average diameter between 3 ångströms and 11 ångströms, advantageously between 4 ångströms and 10 ångströms, preferably between 5 ångströms and 10 ångströms. The adsorbent may also contain noble metals such as silver, platinum, palladium, ruthenium, or rhodium; preferably silver. The adsorbent may also be a polymer and contain these metals, in particular silver. This step may therefore be carried out after step d) and before step e), or after step e). The adsorption step may for example make it possible to remove one or more of said hydrofluorocarbons or make it possible to remove any water present in small amounts.

According to another embodiment, step e) is carried out by cold separation. In this case, said stream A is cooled to a temperature such that said at least one unsaturated fluorinated hydrocarbon is in liquid form and thus formed said stream B1. Thus, the other constituents of the stream A having a boiling point lower than that of said at least one unsaturated fluorinated hydrocarbon are in gaseous form and are removed by degassing. This may be useful for removing gases such as oxygen, nitrogen or carbon dioxide that may be present in the stream A. Said stream B1 may then be reheated to a temperature such that said at least one unsaturated fluorinated hydrocarbon is in gaseous form while keeping the other constituents possibly present in said stream B1 in liquid form. Said at least one unsaturated fluorinated hydrocarbon is thus recovered with a high degree of purity.

According to another embodiment, step e) may be carried out in a pressurized distillation device comprising at least one or more rotating packed beds. In this case, said stream A is compressed and optionally cooled to a temperature such that said at least one fluorinated hydrocarbon is in liquid form. Said stream A thus compressed and optionally cooled is distilled in a pressurized distillation device comprising one or more rotating packed beds in order to form and recover a stream B1 as defined in the present application. The speed of said at least one rotating packed bed is preferably from 100 to 3000 rpm, advantageously from 200 to 2500 rpm, preferably from 500 to 2000 rpm. In this case, step e) is preferably carried out at a pressure of from 2 to 200 bar absolute, preferably from 5 to 100 bar absolute.

The invention claimed is:

1. A process for recovering and upgrading unsaturated fluorinated hydrocarbons, comprising the steps of:
    a) providing a foam M1 consisting of pores containing a composition C1 comprising at least one unsaturated fluorinated hydrocarbon;
    b1) optionally grinding or compressing said foam M1 provided in step a) to form a ground foam or a compressed foam;
    b2) optionally recovering at least a portion of said composition C1 released during step b1), wherein released composition C1 is in a gaseous phase;
    c) depolymerizing or dissolving said foam M1 provided in step a) or said ground or compressed foam obtained in step b1);
    d) recovering at least a portion of said composition C1 released during step c), wherein released composition C1 is in a gaseous phase, and optionally mixing it with said at least a portion of the composition C1 recovered in step b2) to form a stream A comprising at least one unsaturated fluorinated hydrocarbon; and
    e) recovering and separating said stream A formed in step d) into a plurality of streams of which at least one stream B1 comprises said at least one unsaturated fluorinated hydrocarbon.

2. The process as claimed in claim 1, wherein the unsaturated fluorinated hydrocarbon comprises three or four carbon atoms.

3. The process as claimed in claim 1, wherein said unsaturated fluorinated hydrocarbon contains a single carbon-carbon double bond.

4. The process as claimed in claim 1, wherein said foam M1 consists of a polymer selected from the group consisting of polyurethane, polyolefin, poly(methyl methacrylate), polyhydroxyalkanoate, polylactic acid, polyimide, poly(vinyl chloride), poly(ethylene/vinyl acetate), poly(etherimide), poly(methacrylimide), polycarbonate, polystyrene, and a mixture thereof.

5. The process as claimed in claim 1, wherein said foam M1 provided in step a) consists of polystyrene; and step c) is carried out in the presence of an organic solvent capable of dissolving the polystyrene or step c) is carried out by thermal depolymerization of the polystyrene.

6. The process as claimed in claim 1, wherein said foam M1 provided in step a) consists of polyurethane and step c) is carried out by an alcoholysis or hydrolysis or ammonolysis or aminolysis reaction.

7. The process as claimed in claim 1, wherein step c) results in the formation of polyol compounds, the latter being recovered, purified and recycled into a process for the production of polyurethane.

8. The process as claimed in claim 1, wherein step e) of separating said stream is carried out by distillation, azeotropic distillation, pressurized distillation, extractive distillation, cold separation, absorption in a solvent, or a combination thereof.

9. The process as claimed in claim 1, wherein said stream A is subjected to a step of adsorption prior to step e) or said stream B1 is subjected to a step of adsorption after step e).

10. The process as claimed in claim 1, wherein said at least one unsaturated fluorinated hydrocarbon included in said composition C1 is selected from the group consisting of 3,3,3-trifluoropropene, 2,3,3,3-tetrafluoropropene, (E/Z)-1,3,3,3-tetrafluoropropene, (E/Z)-1,2,3,3,3-pentafluoropropene, 2-chloro-3,3,3-trifluoropropene, 1-chloro-3,3,3-trifluoropropene, 1,1-dichloro-3,3,3-trifluoropropene and 1,2-dichloro-3,3,3-trifluoropropene, (E/Z)-1,1,1,4,4,4-hexafluorobut-2-ene, 2,4,4,4-tetrafluorobut-1-ene, and mixtures thereof.

11. The process as claimed in claim 10, wherein said composition C1 also comprises a hydrofluorocarbon other than said at least one unsaturated fluorinated hydrocarbon, an alkane, methyl formate, an inert gas, an alcohol, an ether, a fluorinated ether, an unsaturated fluorinated ether, a ketone, a fluoroketone, a chlorofluorocarbon or water, or a mixture thereof.

12. The process as claimed in claim 11, wherein said hydrofluorocarbon other than said at least one unsaturated fluorinated hydrocarbon is selected from the group consisting of difluoromethane (HFC-32), fluoroethane (HFC-161), 1,2-difluoroethane (HFC-152), 1,1-difluoroethane (HFC-152a), 1,1,2-trifluoroethane (HFC-143), 1,1,1-trifluoroethane (HFC-143 a), 1,1,2,2-tetrafluoroethane (HFC-134), 1,1,1,2-tetrafluoroethane (HFC-134a), 1,1,1,2,2-pentafluoroethane (HFC-125), 1,1,1,3,3-pentafluoropropane (HFC-245fa), 1,1,1,3,3,3-hexafluoropropane (HFC-236fa), 1,1,2,3,3,3-hexafluoropropane (HFC-236ea), 1,1,1,3,3-pentafluorobutane (HFC-365mfc), and 1,1,1,2,3,3,3-heptafluoropropane (HFC-227ea).

13. The process as claimed in claim 11, wherein said chlorofluorocarbon is selected from the group consisting of trichlorofluoromethane, dichlorodifluoromethane, trichlorotrifluoroethane, dichlorotetrafluoroethane and chloropentafluoroethane.

14. The process as claimed in claim 1, wherein said stream A comprises a content of said at least one fluorinated hydrocarbon of between 50% and 99% by volume, based on the total volume of said stream A.

15. The process as claimed in claim 1, wherein step a) also comprises:
providing a foam M2 consisting of pores containing a composition C2 comprising a hydrofluorocarbon selected from the group consisting of difluoromethane (HFC-32), fluoroethane (HFC-161), 1,2-difluoroethane (HFC-152), 1,1-difluoroethane (HFC-152a), 1,1,2-trifluoroethane (HFC-143), 1,1,1-trifluoroethane (HFC-143a), 1,1,2,2-tetrafluoroethane (HFC-134), 1,1,1,2-tetrafluoroethane (HFC-134a), 1,1,1,2,2-pentafluoroethane (HFC-125), 1,1,1,3,3-pentafluoropropane (HFC-245fa), 1,1,1,3,3,3-hexafluoropropane (HFC-236fa), 1,1,2,3,3,3-hexafluoropropane (HFC-236ea), 1,1,1,3,3-pentafluorobutane (HFC-365mfc), and 1,1,1,2,3,3,3-heptafluoropropane (HFC-227ea), or
providing a foam M3 consisting of pores containing a composition C3 comprising a chlorofluorocarbon selected from the group consisting of trichlorofluoromethane, dichlorodifluoromethane, trichlorotrifluoroethane, and dichlorotetrafluoroethane, chloropentafluoroethane, or
providing a mixture of said foams M2 and M3.

16. The process as claimed in claim 15, wherein the foam M2 and the foam M3 consist of a polymer identical to that of said foam M1.

17. The process as claimed in claim 15, wherein the composition C2 and the composition C3 are devoid of unsaturated fluorinated hydrocarbon.

18. The process as claimed in claim 15, wherein it comprises the steps of:
b1) optionally grinding or compressing said foam M1, said foam M2 and/or said foam M3 provided in step a) to form a ground foam or a compressed foam;
b2) optionally recovering at least a portion of said composition C1 and at least a portion of said composition C2 and/or at least a portion of said composition C3, released during step b1);
c) depolymerizing or dissolving said foam M1 and said foam M2 and/or said foam M3 provided in step a) or said ground or compressed foam obtained in step b1);
d) recovering at least a portion of said composition C1 and at least a portion of said composition C2 and/or at least a portion of said composition C3, released during step c), and optionally mixing them with those recovered in step b2) to form a stream A;
e) recovering and separating said stream A into a plurality of streams of which at least one stream B1 comprises said at least one unsaturated fluorinated hydrocarbon.

19. The process as claimed in claim 18, wherein said stream A comprises a content of said at least one fluorinated hydrocarbon of between 0.1% and 50% by volume, based on the total volume of said stream A.

* * * * *